(12) United States Patent
Petersilka (10) Patent No.: US 10,542,944 B2
(45) Date of Patent: Jan. 28, 2020

(54) SINOGRAM-BASED SCATTERED RAY CORRECTION IN COMPUTER TOMOGRAPHY

(71) Applicant: Siemens Healthcare GmbH, Erlangen (DE)

(72) Inventor: Martin Petersilka, Adelsdorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 303 days.

(21) Appl. No.: 15/704,053

(22) Filed: Sep. 14, 2017

(65) Prior Publication Data
US 2018/0078221 A1    Mar. 22, 2018

(30) Foreign Application Priority Data
Sep. 20, 2016   (DE) .................. 10 2016 217 984

(51) Int. Cl.
| | |
|---|---|
| A61B 6/03 | (2006.01) |
| A61B 6/00 | (2006.01) |
| G01N 23/046 | (2018.01) |
| G06T 11/00 | (2006.01) |
| G06N 3/08 | (2006.01) |

(52) U.S. Cl.
CPC ............ *A61B 6/032* (2013.01); *A61B 6/4014* (2013.01); *A61B 6/5205* (2013.01); *A61B 6/5282* (2013.01); *G01N 23/046* (2013.01); *G06N 3/08* (2013.01); *G06T 11/005* (2013.01);
(Continued)

(58) Field of Classification Search
CPC ..... A61B 6/032; A61B 6/5282; A61B 6/5205; A61B 6/4014; A61B 6/583; A61B 6/5211; A61B 6/4411; G06N 3/08; G06T 11/005; G06T 2211/424; G01N 23/046; G01N 2223/419
See application file for complete search history.

(56) References Cited

U.S. PATENT DOCUMENTS

| | | | |
|---|---|---|---|
| 2007/0253524 A1 | 11/2007 | Bruder et al. | |
| 2008/0240340 A1 | 10/2008 | Bruder et al. | |

(Continued)

FOREIGN PATENT DOCUMENTS

| | | |
|---|---|---|
| DE | 102006019923 A1 | 11/2007 |
| DE | 102007014829 B3 | 9/2008 |

OTHER PUBLICATIONS

German Office Action dated Mar. 29, 2017.

*Primary Examiner* — Michael C Bryant
(74) *Attorney, Agent, or Firm* — Harness, Dickey & Pierce, P.L.C.

(57) ABSTRACT

A method is for scattered ray correction of projection measurement data recorded by a computer tomography system. In an embodiment, the method includes recording, localizing, identifying and correcting. In the recording, projection measurement data is recorded from a plurality of projection angles and the projection measurement data is captured in a sinogram. In the localizing, features in the projection measurement data of the sinogram are localized in a defined angle range about a projection angle. In the identifying, a scatter distribution for the projection angle is identified from the localized features by way of a trained identification algorithm. In the correcting, the projection measurement data of the projection angle is corrected on the basis of the scatter distribution.

18 Claims, 3 Drawing Sheets

(52) U.S. Cl.
CPC ........ *A61B 6/583* (2013.01); *G01N 2223/419* (2013.01); *G06T 2211/424* (2013.01)

(56) References Cited

U.S. PATENT DOCUMENTS

| | | | |
|---|---|---|---|
| 2011/0142316 A1* | 6/2011 | Wang | G06T 11/006 |
| | | | 382/131 |
| 2018/0078221 A1* | 3/2018 | Petersilka | A61B 6/032 |
| 2018/0374245 A1* | 12/2018 | Xu | G06T 11/008 |
| 2019/0108904 A1* | 4/2019 | Zhou | G16H 30/20 |

* cited by examiner

SINOGRAM-BASED SCATTERED RAY CORRECTION IN COMPUTER TOMOGRAPHY

PRIORITY STATEMENT

The present application hereby claims priority under 35 U.S.C. § 119 to German patent application number DE 102016217984.5 filed Sep. 20, 2016, the entire contents of which are hereby incorporated herein by reference.

FIELD

At least one embodiment of the invention generally relates to a method for scattered ray correction of projection measurement data recorded by a computer tomography system, a method for training an identification algorithm for identifying a scatter distribution, a computing unit, a computer tomography system, a computer program, a computer-readable data medium, a training unit, a further computer program and/or a further computer-readable data medium.

BACKGROUND

Computer tomography is an imaging method which is primarily used for medical diagnostics and for examining material. In the context of computer tomography, a radiation source (e.g. an x-ray source) and an associated detector device rotate about an object that is to be examined, in order to record spatially three-dimensional image data. During the rotational movement, measurement data is recorded within an angle sector. The projection measurement data represents a plurality of projections containing information about the attenuation of the radiation by the examination object from various projection angles. These projections allow a two-dimensional sectional image or a three-dimensional volume image of the examination object to be calculated. The projection measurement data is also referred to as raw data and may be preprocessed, e.g. in order to reduce any attenuation intensity differences caused by the detectors. Image data can then be reconstructed from this projection measurement data, e.g. by way of so-called filtered back projection or using an iterative reconstruction method.

In computer tomography, scattered radiation is a primary cause of image artifacts. The influence of the scattered radiation is proportional to the size of the detection surface of the detector device that is used and/or to the number of x-ray sources. When using quantum-counting energy-resolving detector devices, the scattered radiation can influence the spectral recordings, since the energy of the photons emitted by the x-ray source is changed by the scattering process, e.g. Compton scattering. In general, and in particular in the case of integrating, counting and energy-resolving detector devices, the scattered radiation changes in such a way that scattered photons which have not followed the direct path from the x-ray source to the detector device are detected by the detector device. These detected events result in image artifacts in the reconstruction process, which normally assumes that the photon of the detected event has followed the direct path.

In computer tomography, the influence of the scattered radiation can be reduced at least partially by way of suppression using a scattered ray grating, or by modeling the physical effects and making allowances accordingly. Scattered ray gratings can shield the x-ray detector by absorbing scattered photons from the scattered radiation. The scattered ray grating is situated close to the detector device in this case, i.e. between examination object and detector device, for example. This is disadvantageous in that the detective quantum efficiency (DQE) is reduced and the manufacturing costs for the scattered ray grating are significant.

Focusing and precise alignment of the scattered ray grating with the x-ray source are also necessary. This makes it harder to use a plurality of x-ray sources or a plurality of x-ray focal points with different geometric arrangements, e.g. in computer tomography systems with minimal inverse geometry or in fourth-generation computer tomography systems having a static detector ring and dynamically mobile focal point. Scattered ray gratings are limited in their effect and cannot completely prevent the detection of scattered radiation.

The calculation of scattered radiation can also be performed in conjunction with scattered ray gratings. The calculation of scattered radiation can be effected by directly modeling the physical processes on the basis of an image or the projection measurement data of a recording by the computer tomography system. Calculation methods based on an image are primarily configured to calculate an exact scattered ray distribution, e.g. using Monte Carlo methods, wherein the computing effort is considerable.

SUMMARY

At least one embodiment of the invention specifies a method for scattered ray correction of projection measurement data recorded by a computer tomography system, a method for training an identification algorithm for identifying a scatter distribution, a computing unit, a computer tomography system, a computer program, a computer-readable data medium, a training unit, a further computer program and/or a further computer-readable data medium, which allow improved sinogram-based scattered ray correction of the projection measurement data.

At least one embodiment is directed to a method for scattered ray correction of projection measurement data recorded by a computer tomography system. At least one embodiment is directed to a method for training an identification algorithm for identifying a scatter distribution. At least one embodiment is directed to a computing unit. At least one embodiment is directed to a computer tomography system. At least one embodiment is directed to a computer program. At least one embodiment is directed to a computer-readable data medium. At least one embodiment is directed to a training unit.

At least one embodiment of the invention relates to a method for scattered ray correction of projection measurement data recorded by a computer tomography system, the method comprising steps for recording, localizing, identifying and correcting. In the recording, projection measurement data is recorded from a plurality of projection angles and the projection measurement data is captured in a sinogram. In the localizing, features in the projection measurement data of the sinogram are localized in a predefined angle range about a projection angle. In the identifying, a scatter distribution for the projection angle is identified from the localized features by way of a trained identification algorithm. In the correcting, the projection measurement data of the projection angle is corrected on the basis of the scatter distribution.

At least one embodiment of the invention further relates to a method for training an identification algorithm for identifying a scatter distribution from projection measurement data recorded by a computer tomography system or from simulated projection measurement data of a recording, the method comprising generating, extracting, localizing, mapping and adapting. In the generating, training data is generated containing a plurality of sinograms and a plurality of scattered ray sinograms based on the sinograms. In the extracting, features in the training data are identified. In the localizing, the features in the plurality of sinograms are localized as a function of the projection angle. In the mapping, the extracted features in a predefined angle range about a predefined projection angle are mapped as a function of the scatter radiation distribution for the predefined projection angle. In the adapting, the identification algorithm is adapted on the basis of the mapped features.

At least one embodiment of the invention further relates to a computing unit for the correction of projection measurement data recorded by a computer tomography system, said computing unit having at least one processor for performing the method according to at least one embodiment of the invention. The method can advantageously execute at least one embodiment of the inventive method for scattered ray correction during or after the recording of projection measurement data.

At least one embodiment of the invention further relates to a computer tomography system comprising a computing unit according to at least one embodiment of the invention. At least one embodiment of the inventive method for scattered ray correction can advantageously be performed directly in the computer tomography system. The computer tomography system can advantageously output image data which has been corrected in respect of scattered rays.

At least one embodiment of the invention further relates to a computer program comprising program code which performs at least one embodiment of the inventive method for scattered ray correction when the computer program is executed on a computer.

At least one embodiment of the invention further relates to a computer-readable data medium containing program code of a computer program which performs at least one embodiment of the inventive method for scattered ray correction when the computer program is executed on a computer. The trained identification algorithm can advantageously be executed on a computer, e.g. in a computing unit of the computer tomography system.

At least one embodiment of the invention further relates to a training unit for training an identification algorithm, comprising at least one processor for performing at least one embodiment of the inventive method for training an identification algorithm. The training unit may comprise a further computing unit, a memory unit, an input interface and an output interface. The training unit can be operated independently of a computer tomography system. The training unit can receive projection measurement data of the recording via the input interface, e.g. by way of a data medium, a cable connection or a wireless connection. The training unit can access projection measurement data of the recording where said data is stored in a cloud, for example. The training unit can be operated on a manufacturing or development site, for example. The training unit can output the identification algorithm, in particular as a program.

At least one embodiment of the invention further relates to a further computer program comprising further program code which performs at least one embodiment of the method for training an identification algorithm when the further computer program is executed on a computer. At least one embodiment of the invention further relates to a further computer-readable data medium containing further program code of a further computer program which performs at least one embodiment of the inventive method for training the identification algorithm when the further computer program is executed on a computer.

At least one embodiment of the invention further relates to a computing unit for correcting projection measurement data recorded by a computer tomography system, comprising:

at least one processor, configured to:
        record projection measurement data from a plurality of projection angles and capture the projection measurement data in a sonogram,
        localize features in the projection measurement data of the sinogram in an angle range about a projection angle,
        identify a scatter distribution for the projection angle from the localized features by way of a trained identification algorithm, and
        correct the projection measurement data of the projection angle on the basis of the identified scatter distribution.

At least one embodiment of the invention further relates to a computer tomography system comprising the computing unit.

At least one embodiment of the invention further relates to a non-transitory memory storing a computer program comprising program code for performing at least one embodiment of the method when the computer program is executed on a computer.

At least one embodiment of the invention further relates to a non-transitory computer-readable data medium containing program code of a computer program for performing at least one embodiment of the method when the computer program is executed on a computer.

BRIEF DESCRIPTION OF THE DRAWINGS

Example embodiments of the invention are explained in greater detail below with reference to drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for scattered ray correction of projection measurement data recorded by a computer tomography system, the method comprising steps for recording, localizing, identifying and correcting. In the recording, projection measurement data is recorded from a plurality of projection angles and the projection measurement data is captured in a sinogram. In the localizing, features in the projection measurement data of the sinogram are localized in a predefined angle range about a projection angle. In the identifying, a scatter distribution for the projection angle is identified from the localized features by way of a trained identification algorithm. In the correcting, the projection measurement data of the projection angle is corrected on the basis of the scatter distribution.

The inventors have found that by using a trained identification algorithm, which includes a mapping of features in known sinograms, e.g. comprising intensity entries, count entries or/and energy entries for an angle range of projection angles, and a plurality of known scattered ray sinograms, the scatter distribution can be derived from an unknown sinogram of the recording. The scatter distribution can then be used for scattered ray correction of the projection measurement data of the recording. A computer-aided process such as machine learning can be used for mapping. The computer-aided process can have two phases. A general training phase can be performed before a recording, in particular. The application phase can comprise the scattered ray correction of recorded projection measurement data.

The recording comprises the recording of projection measurement data by a computer tomography system, projection measurement data being recorded from a plurality of projection angles. The projection measurement data of a projection angle can comprise in particular intensity entries, count entries or/and energy entries for a plurality of detector elements of the detector device. The plurality of detector elements can take the form of a detector row comprising a plurality of detector elements arranged in one dimension, or a plurality of detector rows, in particular a two-dimensional arrangement of detector elements. A projection angle can be understood to be a rotation angle of the x-ray tube/detector system. A plurality of projection angles comprises a plurality of projection angles which differ at least partly from each other.

Furthermore, the projection measurement data can additionally be recorded from a plurality of projection angles in different positions along the rotational axis, and the position along the rotational axis can be adjusted by moving the patient couch, for example. The projection measurement data from a plurality of projection angles may comprise projection measurement data from various rotation angles of the x-ray tube/detector system and/or positions along the rotational axis. The projection measurement data of a plurality of projection angles is captured in a sinogram. The projection measurement data may be captured in chronological sequence in the sinogram, e.g. according to the timing order during the recording. The sinogram can be stored in a memory unit.

In the localizing, features in the projection measurement data of the sinogram are localized in a predefined angle range about a projection angle, e.g. by way of an identification algorithm or/and a database. The identification algorithm is able to access the database. In the localizing, the projection measurement data can be searched for features in a predefined angle range about a projection angle, in particular an individual projection angle. In particular, the relative arrangement or/and position of features in the projection measurement data can be checked. In particular, the features can take the form of intensity entries, count entries or/and energy entries in this case. The angle range is a range of a plurality of, in particular consecutive, projection angles of a recording. The scattered ray correction can be performed for an individual projection angle of the recording. The angle range, e.g. $[\alpha-\Delta\alpha1, \alpha+\Delta\alpha2]$, about the projection angle $\alpha$ is predefined, e.g. on the basis of empirical values, properties of the examination object, projection angles or other parameters. The angle range may be disposed symmetrically or asymmetrically about the projection angle.

The scattered ray correction can be performed for a plurality of projection angles in parallel or consecutively. At least one embodiment of the inventive method and the scattered ray correction can be performed after or during the recording. For each projection angle, features can be localized in a predefined angle range about each projection angle. The angle ranges may vary for different projection angles or/and different positions along the rotational axis or/and different recordings. The system architecture may be taken into consideration when selecting the features or/and the angle ranges, e.g. in order to utilize the capability of the system in an optimal manner.

In the identifying, a scatter distribution for the projection angle is identified from the localized features by way of a trained identification algorithm. The identification algorithm may include assignment rules, a neural network, a system, a learning transfer method or an algorithm which is based on a database or on mathematical functions or equations. The trained identification algorithm can be created or improved or adapted on the basis of known or previously analyzed data. A scatter distribution can be identified for a plurality of projection angles.

In particular, a scatter distribution can be identified for each projection angle. For example, the scatter distribution can be identified via a regressor of a trained neural network, which regressor can be applied to the localized features in the projection measurement data in the predefined angle range. For example, identification can mean that in the projection measurement data in the angle range, features such as e.g. a geometric arrangement or distribution are recognized on the basis of e.g. intensity entries, count entries or/and energy entries from previously analyzed projection measurement data or training data, and the detection of scattered photons can be inferred therefrom. The localized features can relate unambiguously or with qualified probability to an entry in the scatter distribution.

In the localizing or/and identifying, it is possible to access e.g. all projection angles in the predefined angle range. As a result, geometric arrangements from the projection measurement data of the projection angles in the predefined angle range are known. From the features, it is possible to infer intensity entries, count entries or/and energy entries which were caused by scattered photons.

In the correcting, the projection measurement data of the projection angle is corrected on the basis of the scatter distribution. The scatter distribution is used to correct the projection measurement data, of the one projection measurement angle in particular. By virtue of the scattered ray correction, the projection measurement data, e.g. captured in a sinogram, is corrected such that events caused by scattered photons, e.g. in the form of an intensity entry, count entry or/and energy entry, from the projection measurement data can be at least partially corrected.

The identification of the scatter distribution can advantageously be particularly accurate or more accurate because three-dimensional information relating to the examination object is known from the projection measurement data in the predefined angle range. The computing effort required to identify the scatter distribution can advantageously be reduced.

For the purpose of at least one embodiment of the inventive method, two-dimensional projection measurement data from a recording in a sinogram is advantageously sufficient for the purpose of identifying the scatter distributions. It is advantageously possible to dispense with resource-intensive calculations based on Monte Carlo methods or similar. Using machine learning processes, statistical methods such as e.g. fuzzy logic, or mapping rules, the three-dimensional geometry of the examination object can be taken into consideration when identifying the scatter distribution.

It is advantageously possible to achieve a faster identification of the scatter distribution, in particular in comparison with forward modeling of scatter processes. It is advantageously possible to achieve a more accurate identification of the scatter distribution. It is advantageously possible to reduce the manufacturing costs of a third-generation multi-row computer tomography system.

At least one embodiment of the inventive method for scatter correction can advantageously be applied in computer tomography systems with minimal inverse geometry, e.g. with two or three focal points. It is advantageously possible to use fourth-generation computer tomography systems, because e.g. a scattered ray grating is not required.

According to an embodiment of the invention, the trained identification algorithm is based on a machine learning process, a statistical method, a mapping rule or an artificial neural network. The identification algorithm and the contingent database may be based on a machine learning process, a statistical method, a mapping rule or an artificial neural network. Patterns or regularities from the training data can advantageously be applied to the projection measurement data of the recording.

Machine learning processes can be understood to include the artificial generation of knowledge from experience. An artificial system learns from examples in a training phase and is able to generalize after completion of the training phase. The identification algorithm can therefore be adapted. The use of machine learning processes may include the recognition of patterns and regularities in the training data. After the training phase, the identification algorithm is able to localize features in previously unknown projection measurement data, for example. After the training phase, the identification algorithm is able to identify scatter distributions from the localized features in previously unknown projection measurement data, for example.

The statistical method can include fuzzy logic, a self-organizing map, resampling, pattern recognition or support vector machine, for example. On the basis of the experience of the identification algorithm with regard to patterns or regularities, it is advantageously possible to effect an assignment of features to a scatter distribution.

According to an embodiment of the invention, the features comprise width, position, intensity, shape or/and morphology of the attenuation in the projection measurement data. The intensity may comprise a strength of the detected signal in the projection measurement data. The features may comprise annular or elliptical arrangements in the projection measurement data in the predefined angle range. The features may comprise reflexes of a diffuser in the projection measurement data in the predefined angle range. The features may comprise linear arrangements in the projection measurement data in the predefined angle range. The features may be based on intensity entries, count entries or/and energy entries. The features may comprise relative intervals between intensity entries, count entries or/and energy entries. It is advantageously possible to infer the detection of scattered photons from the features. It is advantageously possible to derive patterns or regularities from the features. The morphology of attenuation structures can take the form of connected attenuation regions or a plurality of separate attenuation regions.

According to an embodiment of the invention, the scatter distribution comprises intensity entries, count entries or/and energy entries of scattered photons. The scatter distribution may comprise e.g. only intensity entries, count entries or/and energy entries for the one projection angle. The scatter distribution may comprise e.g. intensity entries, count entries or/and energy entries for at least the one projection angle. The scatter distribution may comprise e.g. intensity entries, count entries or/and energy entries for a plurality of projection measurement angles, e.g. for all projection measurement angles of the angle range. The intensity entries, count entries or/and energy entries of the scattered photons may correspond to e.g. the intensity entries, count entries or/and energy entries of the features. The intensity entries, count entries or/and energy entries of the scattered photons may correspond in particular to the intensity entries, count entries or/and energy entries from known scatter distributions which are associated with the localized features. It is advantageously possible easily to correct the projection measurement data on the basis of the scatter distribution, e.g. using a mathematical operation.

According to an embodiment of the invention, the correcting comprises a mathematical operation. The mathematical operation may comprise a step for changing, subtracting, adding, multiplying or dividing, for example. The correcting of number entries in the projection measurement data may comprise subtracting, for example. The correcting can preferably comprise a subtracting. It is advantageously possible to correct the projection measurement data easily and with little computing effort.

At least one embodiment of the invention further relates to a method for training an identification algorithm for identifying a scatter distribution from projection measurement data recorded by a computer tomography system or from simulated projection measurement data of a recording, the method comprising generating, extracting, localizing, mapping and adapting. In the generating, training data is generated containing a plurality of sinograms and a plurality of scattered ray sinograms based on the sinograms. In the extracting, features in the training data are identified. In the localizing, the features in the plurality of sinograms are localized as a function of the projection angle. In the mapping, the extracted features in a predefined angle range about a predefined projection angle are mapped as a function of the scatter radiation distribution for the predefined projection angle. In the adapting, the identification algorithm is adapted on the basis of the mapped features.

The method for training can be referred to as the training phase. In the generating, training data is generated. The generating can preferably be the first step. The training data comprises a plurality of sinograms and a plurality of scattered ray sinograms. An associated scattered ray sinogram can be present for each sinogram. A scattered ray sinogram can be generated for each sinogram. The scattered ray sinogram can comprise intensity entries, count entries or/and energy entries of scattered photons. The entries of the scattered ray sinogram can be included in the associated sinogram. The difference between sinogram and scattered ray sinogram can be a sinogram which is pruned of scatter effects.

The training data can be based on e.g. numerical anthropomorphic phantoms of various sizes or recordings of examination objects. A sinogram can contain projection measurement data from a recording of an examination object or from a computer-based forward projection. A scattered ray sinogram contains entries of the scattered photons, which can be obtained e.g. by way of Monte Carlo methods on the basis of input images or sinograms, in particular in conjunction with the detection via the detector device. The scattered ray sinograms can be referred to as fundamental truth.

In the extracting, features in the sinograms and in the (in particular associated) scattered ray sinograms are identified or extracted. In the localizing step, the spatial arrangement or position of the features in the sinogram can be localized as a function of the projection angle. It is advantageously possible to extract realistic three-dimensional information about the examination object or phantom. It is particularly advantageous that three-dimensional information about the examination object can allow more accurate identification of a scatter distribution. The extracting and localizing can be performed simultaneously as a combined step.

The mapping comprises assigning or mapping the extracted features to the fundamental truth. In particular, when assigning the features for the one or individual projection angle, all extracted features in the predefined angle range can be taken into consideration. For example, the angle range can comprise 180°. The angle range can assume any suitable value for the system architecture. The mapping or assignment of the features in the predefined angle range to the fundamental truth for an individual projection angle can preferably be based on machine learning processes.

In the adapting, the identification algorithm can be adapted on the basis of the mapped features and by way of a machine learning process, a statistical method, a mapping rule or an artificial neural network. The machine learning process can comprise aspects of data mining. The machine learning process can comprise a symbolic system or a subsymbolic system, e.g. an artificial neural network with or without regression. The machine learning can be monitored, partially monitored, unmonitored, reinforcement or active learning. The machine learning process can comprise batch learning, in which all training data is present concurrently and patterns and regularities are learned by the identification algorithm after processing all of the training data, for example.

The machine learning can comprise a continuous, incremental or sequential learning process, the patterns and regularities being developed in a temporally staggered manner. In the case of continuous, incremental or sequential learning processes, the training data can be lost after one-time execution and adaptation of weightings, for example.

In the case of batch learning or in the case of continuous, incremental or sequential learning processes, the training data can be available in stored format and can be repeatedly accessible. The machine learning process can comprise deep learning processes or shallow learning processes, for example. The knowledge base derived from known training data can advantageously be applied to unknown projection measurement data.

By virtue of the training, the identification algorithm can advantageously allow reliable scatter correction. Projection measurement data from recordings of the method for scattered ray correction can also be used to adapt the identification algorithm, e.g. in order to improve statistical probabilities of the occurrence of features by virtue of an increasingly large database.

At least one embodiment of the invention further relates to a computing unit for the correction of projection measurement data recorded by a computer tomography system, said computing unit having at least one processor for performing the method according to at least one embodiment of the invention. The method can advantageously execute at least one embodiment of the inventive method for scattered ray correction during or after the recording of projection measurement data.

At least one embodiment of the invention further relates to a computer tomography system comprising a computing unit according to at least one embodiment of the invention. At least one embodiment of the inventive method for scattered ray correction can advantageously be performed directly in the computer tomography system. The computer tomography system can advantageously output image data which has been corrected in respect of scattered rays.

At least one embodiment of the invention further relates to a computer program comprising program code which performs at least one embodiment of the inventive method for scattered ray correction when the computer program is executed on a computer.

At least one embodiment of the invention further relates to a computer-readable data medium containing program code of a computer program which performs at least one embodiment of the inventive method for scattered ray correction when the computer program is executed on a computer. The trained identification algorithm can advantageously be executed on a computer, e.g. in a computing unit of the computer tomography system.

At least one embodiment of the invention further relates to a training unit for training an identification algorithm, comprising at least one processor for performing at least one embodiment of the inventive method for training an identification algorithm. The training unit may comprise a further computing unit, a memory unit, an input interface and an output interface. The training unit can be operated independently of a computer tomography system. The training unit can receive projection measurement data of the recording via the input interface, e.g. by way of a data medium, a cable connection or a wireless connection. The training unit can access projection measurement data of the recording where said data is stored in a cloud, for example. The training unit can be operated on a manufacturing or development site, for example. The training unit can output the identification algorithm, in particular as a program.

At least one embodiment of the invention further relates to a further computer program comprising further program code which performs at least one embodiment of the method for training an identification algorithm when the further computer program is executed on a computer. At least one embodiment of the invention further relates to a further computer-readable data medium containing further program code of a further computer program which performs at least one embodiment of the inventive method for training the identification algorithm when the further computer program is executed on a computer.

Figure 1:
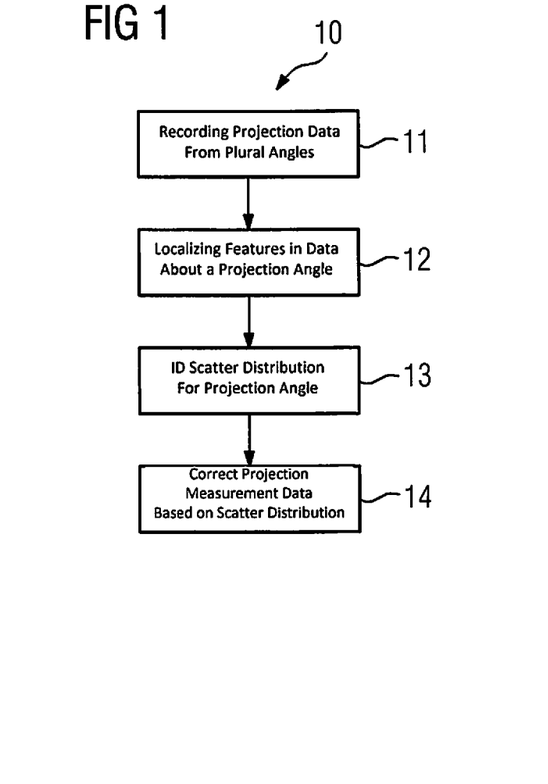
FIG. 1 schematically shows a design of an embodiment of an inventive method for scattered ray correction.

FIG. 1 shows an example embodiment of the inventive method 10 for scattered ray correction. The method 10 for scattered ray correction of projection measurement data of a recording which has been recorded by a computer tomography system comprises steps for recording 11, localizing 12, identifying 13 and correcting 14. In the recording step 11, projection measurement data is recorded from a plurality of projection angles and the projection measurement data is captured in a sinogram. In the localizing step 12, features in the projection measurement data of the sinogram are localized in a predefined angle range about a projection angle. In the identifying step 13, a scatter distribution for the projection angle is identified from the localized features by way of a trained identification algorithm. In the correcting step 14, the projection measurement data of the projection angle is corrected on the basis of the scatter distribution.

The recording 11 comprises the recording of projection measurement data by a computer tomography system, projection measurement data being recorded from a plurality of projection angles. The projection measurement data of a projection angle comprises in particular intensity entries, count entries or/and energy entries for a plurality of detector elements of the detector device. A projection angle is understood to be a rotation angle of the x-ray tube/detector system. A plurality of projection angles comprises a plurality of projection angles which differ at least partly from each other. Furthermore, the projection measurement data can additionally be recorded from a plurality of projection angles in different positions along the rotational axis, and the position along the rotational axis can be adjusted by moving the patient couch, for example. The projection measurement data from a plurality of projection angles may comprise projection measurement data from various rotation angles of the x-ray tube/detector system and/or positions along the rotational axis. The projection measurement data of a plurality of projection angles is captured in a sinogram. The projection measurement data is captured in chronological sequence in the sinogram, e.g. according to the timing order during the recording.

In the localizing step 12, features in the projection measurement data of the sinogram are localized in a predefined angle range about a projection angle, e.g. by way of an identification algorithm. In the localizing step 12, the projection measurement data is searched for features in a predefined angle range about a projection angle, in particular an individual projection angle. In particular, the relative arrangement or/and position of features in the projection measurement data is checked. The angle range is a range of a plurality of, in particular consecutive, projection angles of a recording. The angle range, e.g. $[\alpha-\Delta\alpha 1, \alpha+\Delta\alpha 2]$, about the projection angle $\alpha$ is predefined, e.g. on the basis of empirical values, properties of the examination object, projection angles or other parameters.

In the identifying step 13, a scatter distribution for the projection angle is identified from the localized features by way of a trained identification algorithm. The identification algorithm is preferably based on a machine learning process. The scatter distribution is preferably identified via a regressor of a trained neural network, which regressor can be applied to the localized features in the projection measurement data in the predefined angle range. For example, identification can mean that in the projection measurement data in the angle range, features such as e.g. a geometric arrangement or distribution are recognized on the basis of e.g. intensity entries, count entries or/and energy entries from previously analyzed projection measurement data or training data, and the detection of scattered photons can be inferred therefrom. The localized features relate unambiguously or with qualified probability to an entry in the scatter distribution.

In the correcting step 14, the projection measurement data of the projection angle is corrected on the basis of the scatter distribution. The scatter distribution is used to correct the projection measurement data, of the one projection measurement angle in particular. By virtue of the scattered ray correction, the projection measurement data, e.g. captured in a sinogram, is corrected such that events caused by scattered photons, e.g. in the form of an intensity entry, count entry or/and energy entry, from the projection measurement data are at least partially corrected.

Figure 2:
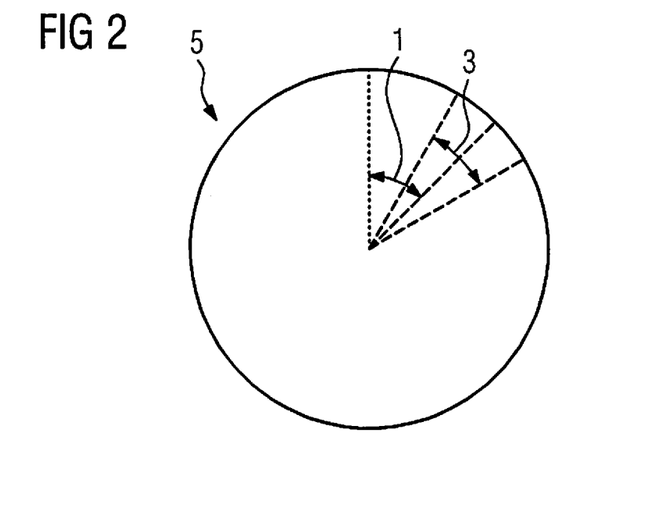
FIG. 2 schematically shows a design of a predefined angle range about a projection angle.

FIG. 2 shows an example embodiment of the predefined angle range 3 about a projection angle 1. The measuring field 5 can be recorded by sampling a plurality of projection angles 1. The projection angle 1 indicates a projection direction which is defined by the rotation angle of the x-ray tube/detector system. The angle range α 3 has the projection angle 1. The angle range α 3 is defined by the range [α−Δα1, α+Δα2]. Δα1 and Δα2 can be defined by the computing capacity within the system architecture. For example, it is possible that Δα1=180° and Δα2=0 (not shown).

Figure 3:
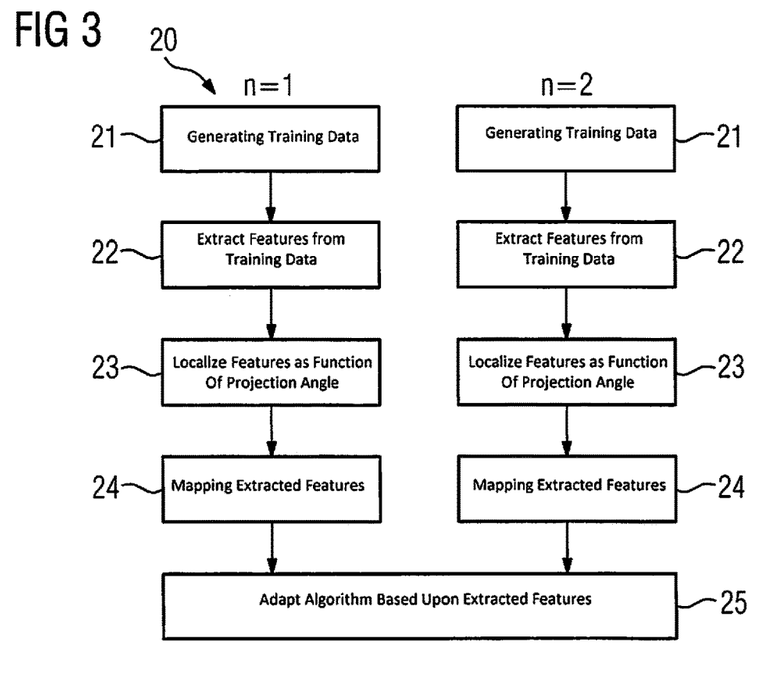
FIG. 3 schematically shows a design of an inventive method for training an identification algorithm according to a first embodiment variant.

FIG. 3 shows an example embodiment of the inventive method 20 for training an identification algorithm according to a first embodiment variant. The method 20 for training an identification algorithm for identifying a scatter distribution from projection measurement data P1, P2, P3 recorded by a computer tomography system or from simulated projection measurement data of a recording has steps for generating 21, extracting 22, localizing 23, mapping 24 and adapting 25. In the generating step 21, training data is generated containing a plurality of sinograms and scattered ray sinograms based on the sinograms. In the extracting step 22, features are extracted from the training data. In the localizing step 23, the features in the plurality of sinograms are localized as a function of the projection angle. In the mapping step 24, the extracted features in a predefined angle range about a predefined projection angle are mapped as a function of the scatter radiation distribution for the predefined projection angle. In the adapting step 25, the identification algorithm is adapted on the basis of the mapped features.

In the generating step 21, training data is generated. The generating step 21 is the first step. The training data comprises a plurality of sinograms and scattered ray sinograms. A scattered ray sinogram is generated for each sinogram. The scattered ray sinogram comprises intensity entries, count entries or/and energy entries of scattered photons. The entries of the scattered ray sinogram are included in the associated sinogram.

The training data is based on e.g. numerical anthropomorphic phantoms of various sizes or recordings of examination objects. A sinogram contains projection measurement data from a recording of an examination object or from a computer-based forward projection. A scattered ray sinogram contains entries of the scattered photons, which can be obtained e.g. by way of Monte Carlo methods on the basis of input images or sinograms, in particular in conjunction with the detection via the detector device. The scattered ray sinograms are referred to as fundamental truth.

In the extracting step 22, features are extracted from the sinograms and the scattered ray sinograms. In the localizing step 23, the spatial arrangement or position of the features in the sinogram are localized as a function of the projection angle.

The mapping step 24 comprises assigning the extracted features to the fundamental truth. In particular, when assigning the features for the one or individual projection angle, all extracted features in the predefined angle range are taken into consideration. For example, the angle range comprises 180°. The angle range can assume any suitable value for the system architecture. The mapping 24 or the assignment of the features in the predefined angle range to the fundamental truth for an individual projection angle is preferably based on machine learning processes. The steps for generating 21, extracting 22, localizing 23 and mapping 24 are performed in parallel for a plurality of training data sources, e.g. for two training data sources n=1 and n=2 as shown.

In the adapting step 25, the identification algorithm is adapted on the basis of the mapped features and by way of a machine learning process, a statistical method, a mapping rule or an artificial neural network. The machine learning process comprises a symbolic system or a subsymbolic system, e.g. an artificial neural network with or without regression. The machine learning comprises monitored, partially monitored, unmonitored, reinforcement or active learning. The machine learning process comprises batch learning, in which all training data is present concurrently and patterns and regularities are learned by the identification algorithm after processing all of the training data, for example. In the case of batch learning, the training data is available in stored format and can be accessed repeatedly.

Figure 4:
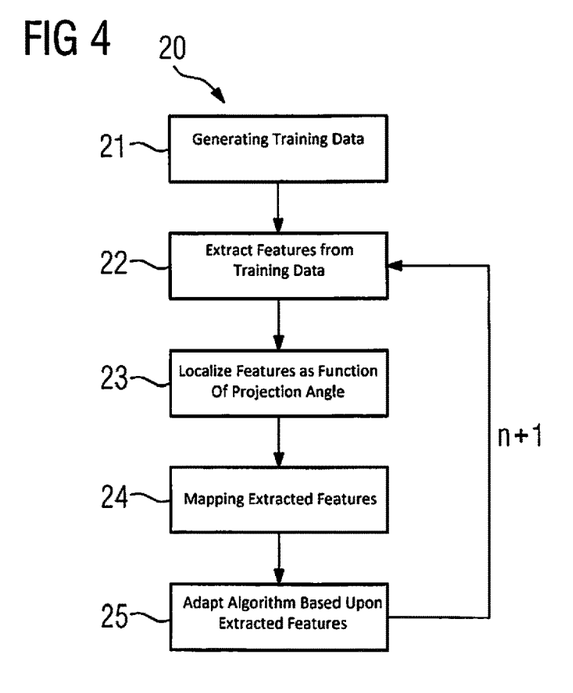
FIG. 4 schematically shows a design of an inventive method for training an identification algorithm according to a second embodiment variant.

FIG. 4 shows an example embodiment of the inventive method 20 for training an identification algorithm according to a second embodiment variant. The method 20 is performed in a plurality of iterations, wherein the first iteration can be referred to as n=1 and all further iterations as n+1. An adaptation 25 takes place in each iteration. The adapted identification algorithm is used in the following iteration n+1. The machine learning comprises a continuous, incremental or sequential learning process, the patterns and regularities being developed in a temporally staggered manner. In the case of continuous, incremental or sequential learning processes, the training data is lost after one-time execution and e.g. adaptation of weightings, or the training data is available in stored format and is repeatedly accessible.

Figure 5:
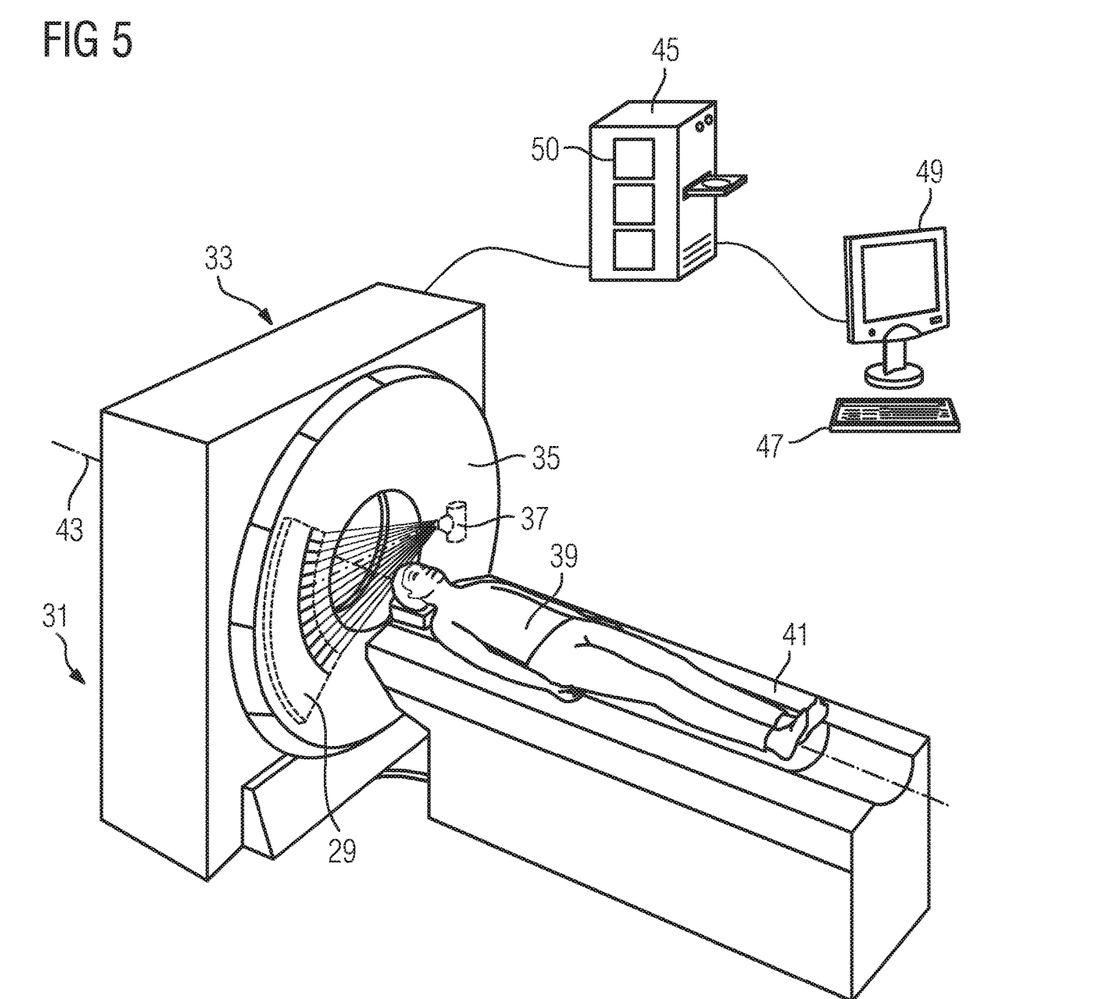
FIG. 5 schematically shows a design of embodiment of an an inventive computer tomograph.

FIG. 5 shows an example embodiment variant of the inventive computer tomography system 31 for executing the inventive method for scattered ray correction. The computer tomography system 31 includes a gantry 33 with a rotor 35. The rotor 35 comprises an x-ray source 37 and the detector device 29. The examination object 39 is supported on the patient couch 41 and can be moved along the rotational axis z 43 through the gantry 33. A computing unit 45 is used for control purposes and to calculate the sectional images, and to perform the inventive method. An input device 47 and an output device 49 are connected to the computer unit 45.

Although the invention is illustrated in detail with reference to the preferred example embodiment, the invention is not restricted by the examples disclosed herein, and other variations may be derived therefrom by a person skilled in the art without thereby departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for correction of projection measurement data recorded by a computer tomography system, comprising:
    recording projection measurement data from a plurality of projection angles and capturing the projection measurement data in a sinogram;
    localizing features in the projection measurement data of the sinogram in an angle range about a projection angle;
    identifying a scatter distribution for the projection angle from the localized features by way of a trained identification algorithm; and
    correcting the projection measurement data of the projection angle on the basis of the identified scatter distribution.

2. The method of claim 1, wherein the trained identification algorithm is based on a machine learning process, a statistical method, a mapping rule, mathematical functions or an artificial neural network.

3. The method of claim 2, wherein the features include at least one of width, position, intensity, shape and morphology of the attenuation in the projection measurement data.

4. The method of claim 2, wherein the scatter distribution includes at least one of intensity entries, count entries and energy entries of scattered photons.

5. The method of claim 2, wherein the correcting includes a mathematical operation.

6. A non-transitory computer-readable data medium containing program code of a computer program for performing the method of claim 2 when the computer program is executed on a computer.

7. The method of claim 1, wherein the features include at least one of width, position, intensity, shape and morphology of the attenuation in the projection measurement data.

8. The method of claim 7, wherein the scatter distribution includes at least one of intensity entries, count entries and energy entries of scattered photons.

9. The method of claim 1, wherein the scatter distribution includes at least one of intensity entries, count entries and energy entries of scattered photons.

10. The method of claim 1, wherein the correcting includes a mathematical operation.

11. A non-transitory memory storing a computer program comprising program code for performing the method of claim 1 when the computer program is executed on a computer.

12. A non-transitory computer-readable data medium containing program code of a computer program for performing the method of claim 1 when the computer program is executed on a computer.

13. A method for adapting an identification algorithm for identifying a scatter distribution from projection measurement data recorded by a computer tomography system or from simulated projection measurement data, the method comprising:
    generating training data comprising a plurality of sinograms and a plurality of scattered ray sinograms based on the sinograms;
    extracting features in the training data;
    localizing the features in the plurality of sinograms as a function of a projection angle;
    mapping the localized features in an angle range about the projection angle as a function of scatter radiation distribution for the projection angle; and
    adapting the identification algorithm based upon the mapped features.

14. A training unit for training an identification algorithm, comprising at least one processor for performing the method of claim 13.

15. A non-transitory memory storing a computer program comprising program code for performing the method of claim 13 when the computer program is executed on a computer.

16. A non-transitory computer-readable data medium containing program code of a computer program for performing the method of claim 13 when the computer program is executed on a computer.

17. A computing unit for correcting projection measurement data recorded by a computer tomography system, comprising:
    at least one processor, configured to:
        record projection measurement data from a plurality of projection angles and capture the projection measurement data in a sonogram,
        localize features in the projection measurement data of the sinogram in an angle range about a projection angle,
        identify a scatter distribution for the projection angle from the localized features by way of a trained identification algorithm, and
        correct the projection measurement data of the projection angle on the basis of the identified scatter distribution.

18. A computer tomography system comprising the computing unit of claim 17.

* * * * *